(12) United States Patent
Hu (10) Patent No.: US 8,121,375 B2
(45) Date of Patent: Feb. 21, 2012

(54) METHODS AND DEVICES FOR PRODUCING THE PARAMETERS OF THE BRAIN TISSUES AND ASSESSING DATA OF THE SUITABILITY FOR THROMBOLYSIS OF A PATIENT

(75) Inventor: Qingmao Hu, Shenzhen (CN)

(73) Assignee: Shenzhen Institute of Advanced Technology, Shenzhen (CN)

( * ) Notice: Subject to any disclaimer, the term of this patent is extended or adjusted under 35 U.S.C. 154(b) by 559 days.

(21) Appl. No.: 12/341,287

(22) Filed: Dec. 22, 2008

(65) Prior Publication Data

US 2010/0014727 A1    Jan. 21, 2010

(30) Foreign Application Priority Data

Jul. 21, 2008  (CN) .......................... 2008 1 0142643

(51) Int. Cl.
 *G06K 9/00* (2006.01)
(52) U.S. Cl. ........................................ 382/131; 382/128
(58) Field of Classification Search .................. 382/128, 382/131; 128/922
See application file for complete search history.

(56) References Cited

U.S. PATENT DOCUMENTS

2009/0129649 A1* 5/2009 Djeridane ..................... 382/131
2009/0326360 A1* 12/2009 Baillet et al. .................. 600/410
* cited by examiner

*Primary Examiner* — David Mis
(74) *Attorney, Agent, or Firm* — Rosenberg, Klein & Lee (57) ABSTRACT

This invention provides a method and a device for producing the parameters of the brain tissue of a patient quickly by using suitable magnetic resonance imaging, utilizing image processing and computer technology, achieving parameters pertaining to the infarction and the ischemic penumbra. This invention also provides a method and a device for producing and assessing data of the suitability for thrombolysis of a patient quickly and properly by using suitable magnetic resonance imaging, utilizing image processing and computer technology, achieving parameters pertaining to the infarction and the ischemic penumbra and predicting the suitability for thrombolysis.

30 Claims, 8 Drawing Sheets

METHODS AND DEVICES FOR PRODUCING THE PARAMETERS OF THE BRAIN TISSUES AND ASSESSING DATA OF THE SUITABILITY FOR THROMBOLYSIS OF A PATIENT

FIELD OF THE INVENTION

The present invention relates to a medical imaging technology, in particular, relates to a method and a device for producing the parameters of the brain tissues of a patient utilizing magnetic resonance imaging (MRI).

The present invention also relates to a method and a device for producing and assessing data of the suitability for thrombolysis utilizing magnetic resonance imaging (MRI).

BACKGROUND OF THE INVENTION

According to the Chinese Ministry of Health, stroke is the second cause of mortality and the first cause of disability in China. There are about 600,000 to 700,000 stroke patients in China, 130,000 to 150,000 new stroke patients and about 100,000 patients died of stroke each year. Among those who survived from the initial symptom onset, about 3 quarters of the patients are disabled to some extents, with about 40% being seriously disabled. Each year China spends more than 30 billion RMB for stroke health care.

According to the American Heart Association and American Stroke Association, there are now more than 700,000 new strokes that occur each year, resulting more than 200,000 deaths per year in the Unite States alone. Ischemic stroke accounts for 80% of this total. Stroke is the leading cause of adult disability in North America and the first cause for inpatient Medicare reimbursement for long term adult care. The National Institute of Health (NIH) estimates that stroke costs now exceed $45 billion US dollars in health care per year.

Ischemic stroke is characterized by complex spatial and temporal events evolving over hours or even days. Within the centre or core of the ischemic territory, blood flow deficits, low ATP (adenosine triphosphate) levels and energy stores, ionic disruption and metabolic failure are severe, and cell death progresses in minutes. However, the peripheral zones within the flow-compromised territory—the ischemic penumbra—suffer milder insults due to residual perfusion from collateral blood vessels. During the early stages of vessel occlusion, the penumbra might compromise as much as a third to half the lesion volume, and actively metabolizes glucose. In this preinfarct margin of metabolically and ionically challenged, metastable tissues, cells die more slowly as the penumbra collapses and the lesion expands over time. In the penumbra, active cell death mechanisms are recruited, and targeting these mechanisms provides promising therapeutic approaches. Within the core territory, salvage of rapidly dying brain cells might not be feasible without early reperfusion.

The concept of ischemic penumbra is now more than 20 years old and has become increasingly important as the potential for treating acute ischemic stroke. Perhaps the simplest but most clinically and pharmacologically relevant definition is "ischemic tissue potentially destined for infarction but not yet irreversibly injured and the target of acute therapy". The reliable detection of the ischemic penumbra would provide much important information for both clinicians and researchers.

Positron emission tomography (PET) is the only modality clinically validated to accurately identify infarction and penumbra. However, due to its limited availability and long post-processing time, PET cannot be used clinically to guide acute stroke therapy.

Magnetic resonance diffusion-weighted imaging (DWI) and perfusion-weighted imaging (PWI) are increasingly available at major hospitals worldwide for the acute evaluation of stroke patients. Many groups have evaluated the utility of the mismatch model: DWI can delineate reduced water molecular diffusion as hyperdense regions while PWI can show a larger area of compromised tissue perfusion early after stroke onset; when the PWI lesion volume is at least 1.25 times as large as that of the DWI lesion, there is a mismatch. The mismatch model has shown promising results.

However, it is widely recognized that the mismatch model is at best a crude approximation of the ischemic penumbra because 1) the perfusion techniques and data evaluation are not truly quantitative and vary among centers; 2) magnetic resonance PWI is invasive and time consuming, and has not been approved by health authorities; 3) the thresholds used for defining perfusion abnormalities have not been validated against PET thresholds; and 4) abnormal diffusion regions early after stroke onset can be reversed by timely intervention in both animals and humans. As such, it is believed and demonstrated that the mismatch contains both penumbra as well as oligaemia.

Though appropriate thrombolysis can greatly improve prognosis of patients and save lives, inappropriate thrombolysis could cause death and symptomatic brain hemorrhage. Even with the only 2 reported successful intravenous thrombolysis stroke trials by NINDS (National Institute of Neurological Disorders and Stroke) within 3 to 6 hours after symptom onset, there were 10-fold increased risk of symptomatic brain hemorrhage guided by the mismatch model. It is thus critical 1) to extend the time window so that more ischemic patients can be considered for active intervention through image analysis instead of purely based on time of symptom onset; 2) to build up models that take into account of both the existence of penumbra and the likelihood of reperfusion injury due to thrombolysis such as symptomatic brain hemorrhage.

This invention intends to provide a solution to estimating parameters needed for assessing if the patient is suitable for thrombolysis.

SUMMARY OF THE INVENTION

The object of the present invention is to provide a method and a device for producing the parameters of the brain tissue of a patient quickly by using suitable magnetic resonance imaging, utilizing image processing and computer technology, achieving parameters pertaining to the infarction and the ischemic penumbra.

To accomplish this object, the present invention is characterized by a method for producing the parameters of the brain tissue of a patient. The method comprises: loading diffusion weighted imaging of a patient comprising a T2-weighted image and an apparent diffusion coefficient (ADC) image achieved by calculation; extracting a brain tissue image without non-brain tissues from the T2-weighted image; achieving a core ADC threshold and a transition ADC threshold that could differentiate a core region and a transition region respectively; binarizing the ADC image with the transition ADC threshold according to the brain tissues image to achieve a binarized ADC image; estimating the core region and the transition region in the binarized ADC image; and calculating a plurality of parameters in the core region and the transition region.

The invention is also characterized by a medical device for producing the parameters of the brain tissues of a patient. The device comprising: an input unit loading two diffusion weighted imaging: (1) a T2-weighted image, and (2) an ADC image; an extraction unit extracting a brain tissues image from the T2-weighted image; an image processing unit achieving a core ADC threshold and a transition ADC threshold that could differentiate a core region and a transition region respectively and binarizing the ADC image through the transition ADC threshold according to the brain tissues image to achieve a binarized ADC image; and an estimation unit estimating a core region and a transition region in the binarized ADC image and calculating a plurality of parameters in the core region and the transition region.

Another object of the present invention is to provide a method and a device for producing and assessing data of the suitability for thrombolysis of a patient quickly and properly by using suitable magnetic resonance imaging, utilizing image processing and computer technology, achieving parameters pertaining to the infarction and the ischemic penumbra and predicting the suitability for thrombolysis.

To accomplish this object, the present invention is characterized by a medical device for producing and assessing data of the suitability for thrombolysis of a patient. The device comprises: an input unit loading two diffusion weighted imaging: (1) a T2-weighted image, and (2) an ADC image; an extraction unit extracting a brain tissues image from the T2-weighted image; an image processing unit achieving a core ADC threshold and a transition ADC threshold that could differentiate a core region and a transition region respectively and binarizing the ADC image through the transition ADC threshold according to the brain tissues image to achieve a binarized ADC image; an estimation unit estimating a core region and a transition region in the binarized ADC image and calculating a plurality of parameters in the core region and the transition region; a training database having training samples using suitable patient data; and an output unit assessing the existence of the ischemic tissues to be rescued and the suitability for thrombolysis if the parameters accord with predetermined rules derived from training samples.

The invention is also characterized by a method for producing and assessing data of the suitability for thrombolysis of a patient. The method comprises: loading diffusion weighted imaging of a patient comprising a T2-weighted image and an ADC image; extracting a brain tissue image without non-brain tissues from the T2-weighted image; achieving a core ADC threshold and a transition ADC threshold that could differentiate a core region and a transition region respectively; binarizing the ADC image with the transition ADC threshold according to the brain tissues image to achieve a binarized ADC image; estimating the core region and the transition region in the binarized ADC image; calculating a plurality of parameters in the core region and the transition region; and assessing the existence of the ischemic tissues to be rescued and the suitability for thrombolysis if the parameters accord with predetermined rules derived from training samples.

There are at least three advantages over the existing mismatch method:

There is no need to perform perfusion-weighted imaging (PWI) which is time consuming and invasive. This will shorten the imaging time and save the critical time for decision making, reduce the patient cost and decrease the physical pain of the patient.

The disclosed method of the present invention takes into account of hemorrhage transformation and symptomatic hemorrhage to prevent reperfusion injury, which is considered the most dangerous complications which prevent the thrombolysis from being widely adopted by hospitals, especially those in China.

The rescued time window is not limited to 3 hours or 6 hours. A patient who is admitted within one day and presents positive signs of thrombolysis (i.e., the acute T2 and ADC data being processed to have recommendation of thrombolysis) is recommended for thrombolysis. This will allow more patients to be rescued and will eventually contribute to the decrease in mortality as well as disability.

BRIEF DESCRIPTION OF THE DRAWINGS

Example embodiments of the invention with refinements will be explained hereafter. Examples set forth do not constitute a restriction of the invention. In particular, the size ratios are purely schematic. In the drawings.

DESCRIPTION OF THE PREFERRED EMBODIMENT

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

EXAMPLE 1

The Method for Producing the Parameters of the Brain Tissues of a Patient

The method of the present invention utilizes the Diffusion-Weighted Imaging (DWI) of a ischemic stroke patient, including two volumetric data form diffusion weighted imaging: (1) T2-weighted image (i.e., the DWI with the gradient factor b being 0) denoted as T2(x, y, z), and (2) the ADC image denoted as ADC(x, y, z)), both of which have the same voxel sizes, same coordinate systems, and the same coordinates correspond to the same physical positions, obtained when the patient is admitted to have the acute DWI scan.

Both T2(x, y, z) and ADC(x, y, z) are in 16-bits DICOM format. It is assumed that the voxel sizes in the X, Y, and Z directions are denoted as voxX, voxY, and voxZ, respectively with mm/voxel as their units. Here (x, y, z) are integer coordinates of voxels satisfying $0 \leq x \leq xSize-1$, $0 \leq y \leq ySize-1$, $0 \leq z \leq zSize-1$. The z coordinate is constant on axial, y on coronal, and x on sagittal slices.

Figure 1:
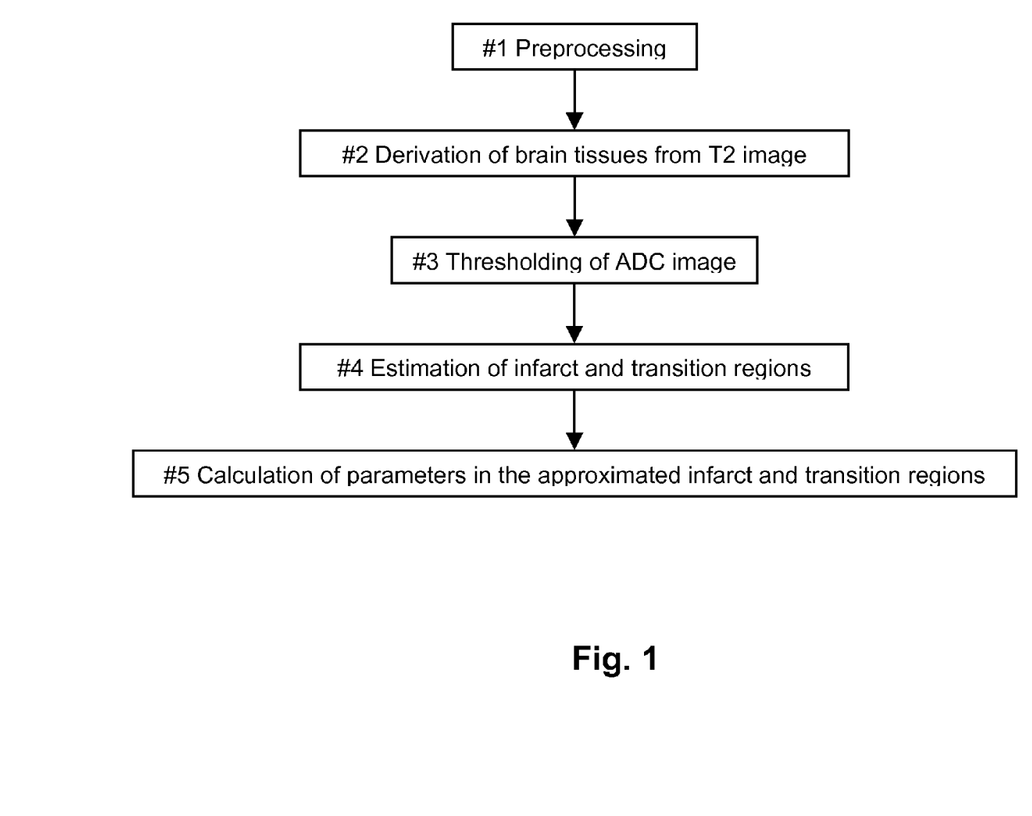
FIG. 1 shows a simplified flowchart of the method for producing the parameters of the brain tissue of a patient according to the present invention.

A method is disclosed to first estimate the core and penumbra (for clarity and avoiding confusion, the penumbra is avoided by using transition region instead) through analyzing T2 and ADC images, with T2 images providing brain tissue information while ADC describing the ischemic extents. Based on the approximated core and transition region, parameters are calculated to quantify the characteristics in the approximated core and transition region to judge if the patient is appropriate for thrombolysis. These parameters cover at least the existence of tissues to be rescued and likelihood to symptomatic brain hemorrhage. The rules of these parameters to evaluate suitability for thrombolysis are derived from training and have been tested with success from real clinical data. FIG. 1 is the flowchart of the method.

Detailed steps are given below.

Step #1: Preprocessing

It comprises loading the original T2 image, loading the original ADC image or the ADC image achieved by calculation, converting the 16-bits data to 8-bit and grayscale normalization.

The ADC(x, y, z) can be calculated as $$ADC(x, y, z) = C \times \log \frac{T2(x, y, z)}{Bh(x, y, z)}$$

Where C is a constant, and Bh(x, y, z) is the diffusion-weighted image with the gradient factor b being 1000 or 1500 s/mm². The calculated ADC can be enhanced through noise removal such as median filtering.

As previously mentioned, the original T2 image and the ADC image are 16-bits data in DICOM format which contains other information pertaining to the imaging procedure and patient particulars. As the T2 grayscale and ADC values of brain tissues are within the range of several hundreds or thousands, it is reasonable to convert the 16-bit image data to 8-bit. Among many ways of conversion, a scheme which is based on percentile is adopted which is not sensitive to few very dark and/or very bright voxels.

To convert, the low and high percentiles are specified which can be set by users or through experience. Suppose the low and high percentiles are $P_l$ and $P_h$, respectively (such as 0.01% and 99.99%, respectively). For T2 image, its grayscale histogram can be calculated and denoted as $hist_{T2}(i)$, where $hist_{T2}(i)$ represents the number of voxels with T2 being i. From $histT_2(i)$, the grayscales $T2_0$ an $T2_1$ corresponding to the low and high percentiles can be derived according to the definition of percentiles:

$$T2_0 = \max_i \left\{ i \left| \sum_{j=0}^{j=i} hist_{T2}(j) \leq xSize * ySize * zSize * P_l \right. \right\} \quad (1)$$

$$T2_1 = \max_i \left\{ i \left| \sum_{j=0}^{j=i} hist_{T2}(j) \leq xSize * ySize * zSize * P_h \right. \right\} \quad (2)$$

With $T2_0$ and $T2_1$, the conversion from the original 16-bit T2(x, y, z) to the 8-bit T2(x, y, z) (denoted as T2_8(x, y, z)) can be calculated $$T2\_8(x, y, z) = \begin{cases} 0, & T2(x, y, z) < T2_0 \\ 255 \times (T2(x, y, z) - T2_0) \div (T2_1 - T2_0), & T2_0 < T2(x, y, z) < T2_1 \\ 255, & T2(x, y, z) > T2_1 \end{cases} \quad (3)$$

The ADC image can be converted into 8-bit data in a similar way, and the converted 8-bit data is denoted as ADC_8(x, y, z).

Step #2: Derivation of Brain Tissues from T2 Image

There are many ways to extract brain from T2-weighted images. Here a scheme which is based on grayscale thresholding and mathematical morphology is given.

Firstly, the 8-bit data T2_8(x, y, z) is clustered into 4 classes with ascending grayscales through fuzzy c-means clustering (FCM) with fuzziness constant being 2. The intensity threshold excluding non-brain tissues is denoted as Th1, which takes the value of the maximum grayscale of the first cluster.

Then the 8-bit data T2_8(x, y, z) is binarized into B1(x, y, z) as following: for any voxel (x0, y0, z0), if T2_8(x0, y0, z0) is not smaller than Th1, then (x0, y0, z0) is set as 1 (i.e., foreground voxel of B1(x, y, z) image); other voxels are set as 0 (i.e., background voxel of B1(x, y, z) image).

Find the largest foreground connected component of B1(x, y, z). This component consists of all voxels which are spatially neighbored and are all foreground voxels of B1(x, y, z).

For B1(x, y, z), only those foreground voxels which are included in the largest connected component are kept as the foreground voxels, other voxels are set to background.

To break the connections between the brain and non-brain voxels, morphological open with square structuring element of side 10 mm are applied to each axial slice of B1(x, y, z). Find the foreground regions of each axial slice of B1(x, y, z) and change holes into foreground (each hole is a background region enclosed by one foreground region).

Figure 3:
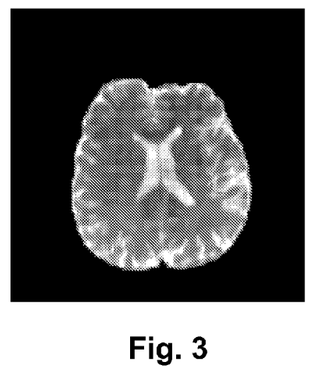
FIG. 3 shows a brain tissues extracting from the T2-weighted image according to FIG. 2.
Figure 4:
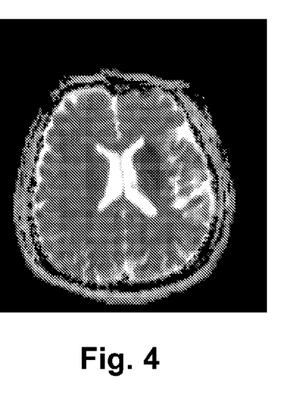
FIG. 4 shows an ADC image of the same patient at the same position as that of FIG. 2.

FIGS. 3 and 4 show, respectively, a T2-weighted axial slice and its corresponding brain tissue after step #2 processing.

Step #3: Thresholding of ADC Image

The binarization of ADC image intends to estimate the infarct and penumbra regions. As Guadagno et al (Guadagno J V, Warburton E A, Aigbirhio F I, Smielewski P, Fryer T D, Harding S, Price C J, Gillard J H, Carpenter T A, Baron J C. Does the acute diffusion-weighted lesion represent penumbra as well as core? A combined quantitative PET/MRI voxel-based study. Journal of Cerebral Blood Flow and Metabolism 2004; 24: 1249-1254) pointed out, even though the ADC values are decreasing from normal to penumbra and from penumbra to infarct regions, there is overlap. Thus it is very hard, if not impossible, to find ADC thresholds that could differentiate the normal, penumbra and infarct regions. Instead of precisely locating the infarct and penumbra regions, here an approximation is achieved through thresholding.

To compensate the normal ADC values of different individuals, the most frequent ADC value of a patient from all its brain tissue derived in step #2 is found, this value $ADC_{max}$ is taken as the reference ADC of this subject and is denoted as $ADC_{ref}$. Alternatively, $ADC_{ref}$ can take value in the neighborhood of $ADC_{max}$, i.e., can be in the range of $[ADC_{max} -5, ADC_{max} +5]$, for instance.

The thresholds to differentiate infarct from penumbra, and penumbra from normal tissues are denoted as $thADC_1$, and $thADC_2$, respectively. They are set as a proportion of $ADC_{ref}$.

$$thADC_1 = P_1 * ADC_{ref} \quad (4)$$

$$thADC_2 = P_2 * ADC_{ref} \quad (5)$$

where $P_1$ and $P_2$ are two constants which can be set according to experience, * denotes multiplication. The recommended ranges for $P_1$ and $P_2$ are [0.55, 0.70] and [0.75, 0.90], respectively.

More generally, the two thresholds can be slice dependent and are denoted as $thADC_1(z)$ and $thADC_2(z)$, respectively. This can be achieved by finding the most frequent ADC of the brain tissues for each axial slice n and replacing $ADC_{ref}$ with $ADC_{ref}(z)$ which takes the value in the neighborhood of the most frequent ADC of the brain in axial slice z.

Step #4: Estimation of a Core Region and a Transition Region

First, the ADC image is binarized as follow $$B\_ADC(x, y, z) = \begin{cases} 1, & ADC\_8(x, y, z) \leq thADC_2(z) \\ 0, & ADC\_8(x, y, z) > thADC_2(z) \end{cases} \quad (6)$$

Then, for B_ADC(x, y, z) set all those background voxels of B1(x, y, z) to 0, which means only those brain tissues with ADC values not greater than $thADC_2(z)$ will be considered as a foreground candidate of B_ADC(x, y, z).

For the derived binarized ADC image B_ADC(x, y, z), all foreground components for different axial slice z could be found. The volume of a component is the number of voxels of the component times voxX*voxY*voxZ. A foreground component will be set to background component of B_ADC(x, y, z) if it is very small in size or close to the skull in the form of the following three conditions: The volume of the foreground component is smaller than a predefined volume $num_0$ (150 mm³ for example). The volume of voxels whose ADC values are smaller than $thADC_1(z)$ is smaller than another predefined volume $num_1$ (15 mm³ for example). The maximum distance of the component to the brain boundary is not smaller than 10 mm, to avoid the partial volume effect close to the skull. When either condition of the 3 is met, the foreground component of B_ADC(x, y, z) is set to background.

For each of the foreground voxel of the B_ADC(x, y, z), check its immediate neighbors in the upper and lower axial slices. If (x0, y0, z0) is a foreground voxel of B_ADC(x, y, z), then the ADC values of (x', y', z') are checked. Here (x', y', z') can take the value of (x0−1, y0−1, z0−1), (x0, y0−1, z0−1), (x0+1, y0−1, z0−1), (x0−1, y0, z0−1), (x0, y0, z0−1), (x0+1, y0, z0−1), (x0−1, y0+1, z0−1), (x0, y0+1, z0−1), (x0+1, y0+1, z0−1), (z0−1, y0−1, z0+1), (x0, y0−1, z0+1), (x0+1, y0−1, z0+1), (x0−1, y0, z0+1), (x0, y0, z0+1), (x0+1, y0, z0+1), (x0−1, y0+1, z0+1), (x0, y0+1, z0+1), (x0+1, y0+1, z0+1). If ADC_8(x', y', z') is not greater than $thADC_2$, then (x', y', z') is set as 1 of B1_ADC(x, y, z). Find all the foreground components of B_ADC(x, y, z) at each axial slice n.

For a foreground component with its volume smaller than a preset volume $num_2$ (15 mm³ for example), it is set to background. The final processed B_ADC(x, y, z) which is a binarized ADC image is denoted as BF_ADC(x, y, z).

For each of the foreground component of BF_ADC(x, y, z), those voxels with ADC values not greater than $thADC_1$ are the approximated infarct voxels while the rest are the approximated penumbra voxels. All the approximated infarct voxels form the approximated core region, while all the approximated penumbra voxels form the transition region.

Figure 2:
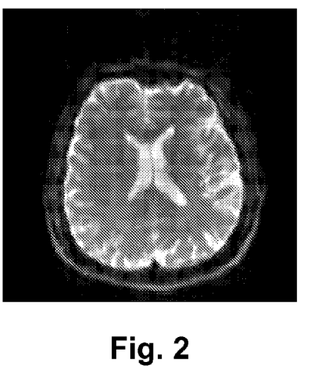
FIG. 2 shows a T2-weighted image.
Figure 5:
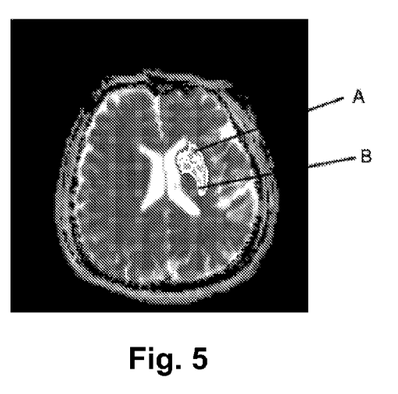
FIG. 5 shows the approximated core and transition regions overlaid on the same axial slice of the ADC image of FIG. 4.

FIGS. 4 and 5 show, respectively, an axial slice of ADC image with the same positions as FIG. 2 from the same patient, and the approximated core denoted as A and transition region denoted as B overlaid on the ADC image.

Step #5: Calculation of Parameters in the Approximated Core and Transition Regions Count the number of voxels of the foreground voxels of BF_ADC(x, y, z) whose ADC values are not greater than $thADC_1$, and denote the number as numCore. Count the number of voxels of the foreground voxels of BF_ADC(x, y, z) whose ADC values are not greater than $thADC_2$ but greater than $thADC_1$, and denote the number as numTR. The volumes of the approximated core and transition regions can be calculated as $$volCore = voxX * voxY * voxZ * numCore \quad (7)$$

$$volTR = voxX * voxY * voxZ * numTR \quad (8)$$

where * denotes multiplication.

The volumes ratio can be calculated as $$volRatio = volTR/volCore \quad (9)$$

Among all the foreground components of BF_ADC(x, y, z), find the components with the maximum and second maximum volumes and denote them as Cmt1(x, y, z) and Cmt2(x, y, z), respectively. The rationale choosing 2 components instead of processing all the components are twofold: 1) small components are more prone to noise, and 2) it takes less time to process less components. Another option may be just to process the maximum foreground component.

1. Calculation of the ADC Gradient of the Transition Region

For Cmt1(x, y, z) and Cmt2(x, y, z), find their internal points. The internal points of Cmt1(x, y, z) are those points (x0, y0, z0), with (x0, y0, z0) belonging to Cmt1(x, y, z), and all its eight neighbors ((x0−1, y0−1, z0), (x0, y0−1, z0), (x0+1, y0−1, z0), (x0−1, y0, z0), (x0+1, y0, z0), (x0−1, y0+1, z0), (x0, y0+1, z0), (x0+1, y0+1, z0)) also belonging to Cmt1 (x, y, z). The internal points of Cmt2(x, y, z) can be determined in the same way.

For each internal point (x0, y0, z0) of Cmt1(x, y, z)/Cmt2 (x, y, z), from ADC_8(x, y, z) find the maximum ADC values of (x0−1, y0, z0), (x0+1, y0, z0), (x0, y0−1, z0), (x0, y0+1, z0) and denote it as max_4(x0, y0, z0); find the maximum ADC values of (x0−1, y0−1, z0), (x0+1, y0−1, z0), (x0−1, y0+1, z0), (x0+1, y0+1, z0) and denote it as max_8(x0, y0, z0). The ADC gradient at (x0, y0, z0) is the maximum of max_4(x0, y0, z0)-ADC_8(x0, y0, z0) and (max_8(x0, y0, z0)-ADC_8(x0, y0, z0))/1.414, and is denoted as grad(x0, y0, z0). When grad(x0, y0, z0) is negative, it is set to 0, i.e., the minimum value of the ADC gradient is 0.

The average ADC gradients of all voxels whose ADC values are in the range of [$thADC_1(z), thADC_2(z)$] for Cmt1(x, y, z) and Cmt2(x, y, z) are denoted as $avgGrad_1$ and $avgGrad_2$, respectively. The average ADC values of all voxels whose ADC values are in the range of [$thADC_1(z), thADC_2(z)$] for Cmt1(x, y, z) and Cmt2(x, y, z) are denoted as $avgTRADC_1$ and $avgTRADC_2$, respectively. The normalized average gradient of all voxels whose ADC values are in the range of [$thADC_1(z), thADC_2(z)$] for Cmt1(x, y, z) and Cmt2(x, y, z)

are denoted as avgGradN$_1$ and avgGradN$_2$, respectively, and are determined by the following formulae, $$avgGradN_1 = avgGrad_1 * C / (ADC_{ref} * avgTRADC_1) \quad (10)$$

$$avgGradN_2 = avgGrad_2 * C / (ADC_{ref} * avgTRADC_2) \quad (11)$$

where C is a constant for normalization which can take a value around 0.73. This normalization is to compensate the difference in average ADC of the approximated transition regions of the two foreground components Cmt1(x, y, z) and Cmt2(x, y, z).

Then the ADC gradient of the transition region is the maximum of avgGradN$_1$ and avgGradN$_2$, $$avgGradN = \max(avgGradN1, avgGradN2) \quad (12)$$

2. Calculation of the Radial Distance of the Approximated Transition Region

For Cmt1(x, y, z) and Cmt2(x, y, z), suppose the numbers of voxels whose ADC values are not greater than thADC$_1$ (z) are N$_{10}$ and N$_{20}$, respectively; the numbers of voxels whose ADC values are in the range of [thADC$_1$ (z), thADC$_2$ (z)] are N$_{11}$ and N$_{21}$, respectively. Then the radial dimensions of the approximated core and transition regions can be approximated $$R_{10} = \mathrm{sqrt}\ (N_{10}/3.1416) \quad (13)$$

$$R_{11} = \mathrm{sqrt}\ ((N_{10}+N_{11})/3.1416) \quad (14)$$

$$R_{20} = \mathrm{sqrt}\ (N_{20}/3.1416) \quad (15)$$

$$R_{21} = \mathrm{sqrt}\ ((N_{20}+N_{21})/3.1416) \quad (16)$$

R$_{10}$ and (R$_{11}$-R$_{10}$) are the approximated radial distances of the approximated core and transition regions of Cmt1(x, y, z), while R$_{20}$ and (R$_{21}$-R$_{20}$) are the approximated radial distance of the approximated core and transition regions of Cmt2(x, y, z).

Then the radial distance of the approximated transition region is the maximum of the radial distance of the approximated transition regions of Cmt1(x, y, z) and Cmt2(x, y, z), $$\delta R = \max(R11\text{-}R11, R21\text{-}R20) \quad (17)$$

3. Calculation of the ADC Change of the Transition Region

The expected ADC change (denoted as δADC) for the approximated transition regions of Cmt1(x, y, z) and Cmt2(x, y, z) are defined as the product of the radial distance and the normalized average gradient of the transition regions, i.e., $$\delta ADC_1 = (R_{11}\text{-}R_{10})/ADC_{ref} * avgGradN_1 \quad (18)$$

$$\delta ADC_2 = (R_{21}\text{-}R_{20})/ADC_{re} * avgGradN_2 \quad (19)$$

Then the ADC change of the transition region is the minimum of δADC$_1$ and δADC$_2$, $$\delta ADC = \min(\delta ADC_1, \delta ADC_2) \quad (20)$$

4. Calculation of the Coefficient of Variation of ADC

The average, standard deviation and coefficient of variation of ADC for all voxels whose ADC values are not greater than thADC$_1$ (z) for Cmt1(x, y, z) are computed and denoted as avgCoreADC$_1$, sdCoreADC$_1$, and cvCoreADC$_1$, with cvCoreADC$_1$=sdCoreADC$_1$/avgCoreADC$_1$.

The average, standard deviation and coefficient of variation of ADC for all voxels whose ADC values are not greater than thADC$_1$ (z) for Cmt2(x, y, z) are computed and denoted as avgCoreADC$_2$, sdCoreADC$_2$, and cvCoreADC$_2$, with cvCoreADC$_2$=sdCoreADC$_2$/avgCoreADC$_2$.

EXAMPLE 2

Figure 6:
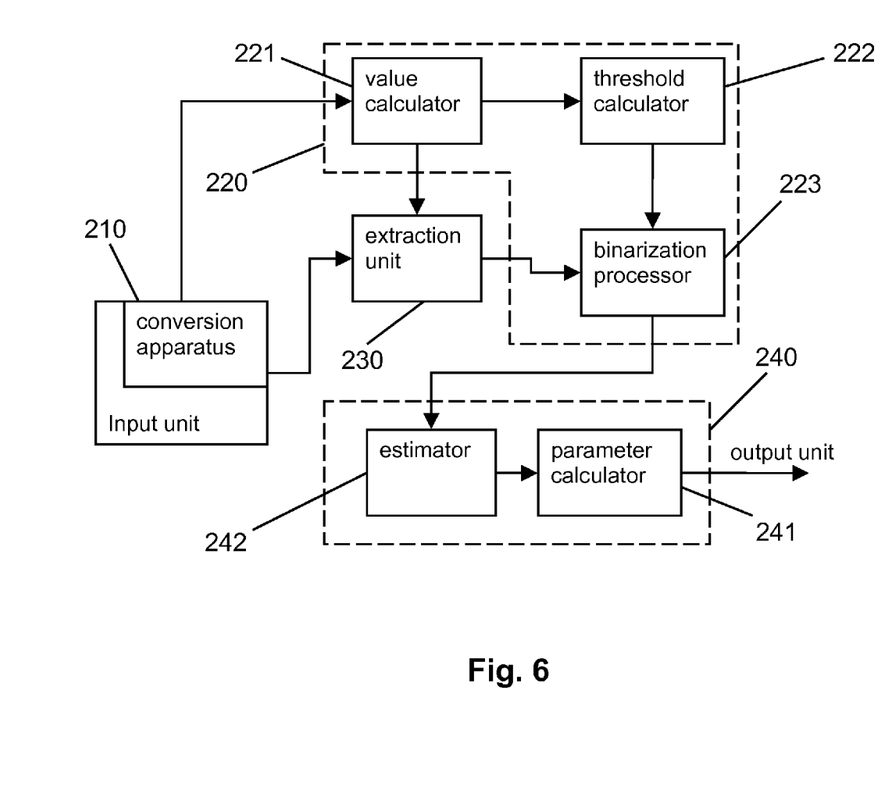
FIG. 6 shows a schematic illustration of the medical device for producing the parameters of the brain tissue of a patient according to the present invention.

The Medical Device Producing the Parameters of the Brain Tissues of a Patient, the Device Comprising Based on the method described above, a medical device comprises at least an input unit 210 and a processing module. The input unit provides interface for inputting the DICOM data of the patients T2(x, y, z) and ADC(x, y, z), and the processing module to perform the processing described in steps 1 to 5.

The input unit 210 has a conversion apparatus converting the image from 16-bit data to 8-bit or 4-bit data, i.e. an apparatus implementing the step #1.

The processing module comprises an extraction unit 230 extracting a brain tissues image from the T2-weighted image, an image processing unit 220 achieving a core ADC threshold and a transition ADC threshold that could differentiate a core region and a transition region respectively and binarizing the ADC image through the transition ADC threshold according to the brain tissues image to achieve a binarized ADC image, and an estimation unit 240 estimating a core region and a transition region in the binarized ADC image and calculating a plurality of parameters in the core region and the transition region.

The image processing unit 220 comprises a value calculator 221, a threshold calculator 222 and a binarization processor 223. The value calculator 221 is connected to the input unit 210 and the extraction unit 230. The value calculator 221 gets a ADC value of the normal brain tissue from the ADC image. The threshold calculator 222 multiplies the ADC value of the normal brain tissue by two constants respectively to achieve a core ADC threshold and a transition ADC threshold that could differentiate a core region and a transition region respectively. The binarization processor 223 binarizes the ADC image through the transition ADC threshold according to the brain tissues image to achieve a binarized ADC image.

The estimation unit 240 comprises an estimator 242 and a parameter calculator 241. The estimator 242 estimates a core region and a transition region in the binarized ADC image. The parameter calculator 241 finds at least one foreground connected component with the maximum volumes in the core region and the transition region and calculates a plurality of parameters in the components.

Figure 7:
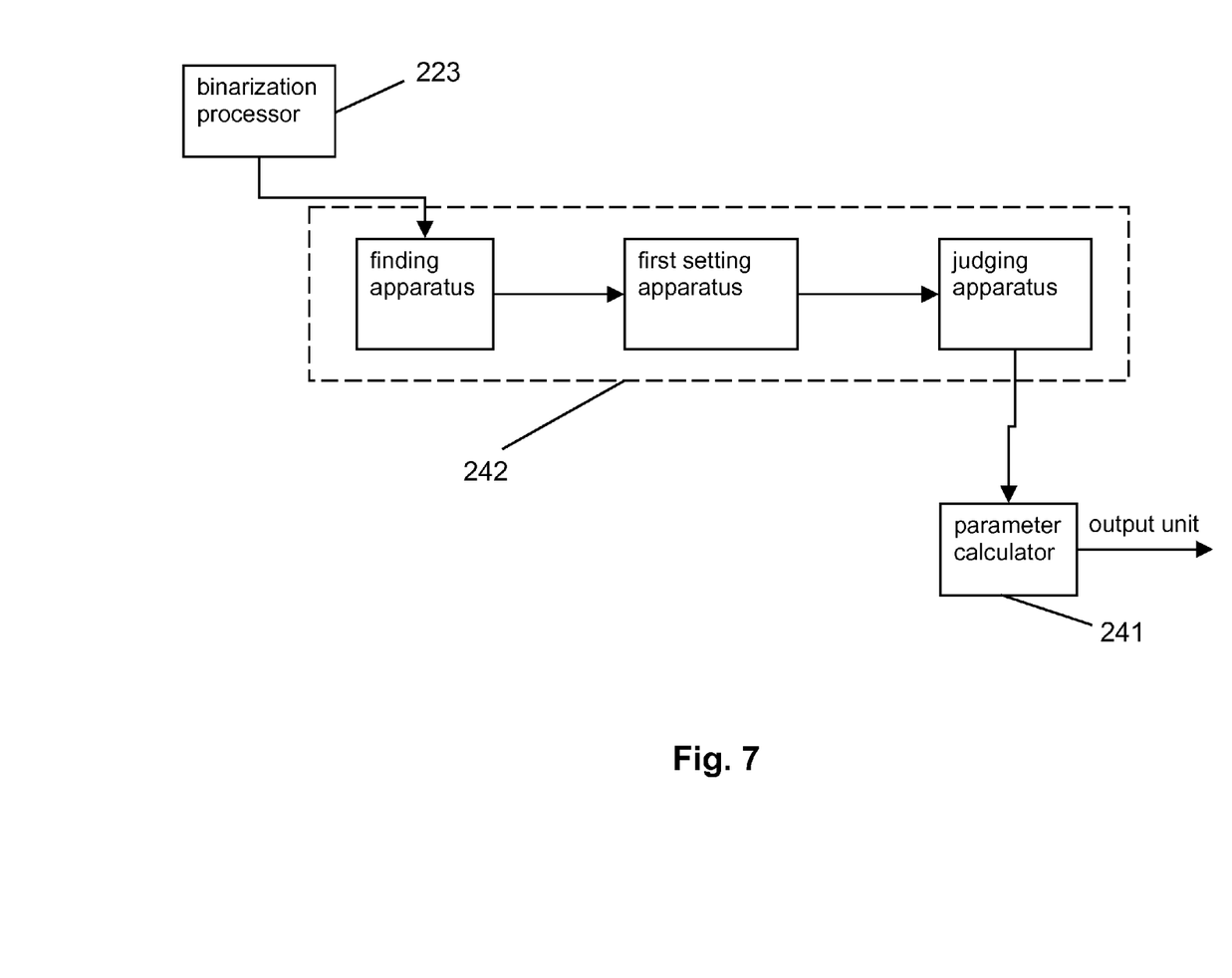
FIG. 7 shows a schematic illustration of the first embodiment of the estimation unit of the medical device of FIG. 6.

As showing in FIG. 7, the estimator 242 comprises a finding apparatus, a first setting apparatus and a judging apparatus. The finding apparatus finds a foreground component in the binarized ADC image of each slice. The first setting apparatus sets a foreground component to a background component if the volume of the foreground component is smaller than a first volume and the volume of voxels whose ADC values are smaller than the core ADC value is smaller than a second predefined volume. The judging apparatus determines those voxels with ADC values smaller than the core threshold forming the core region while those voxels with ADC values smaller than the transition threshold and bigger than the core threshold forming the transition region.

Figure 8:
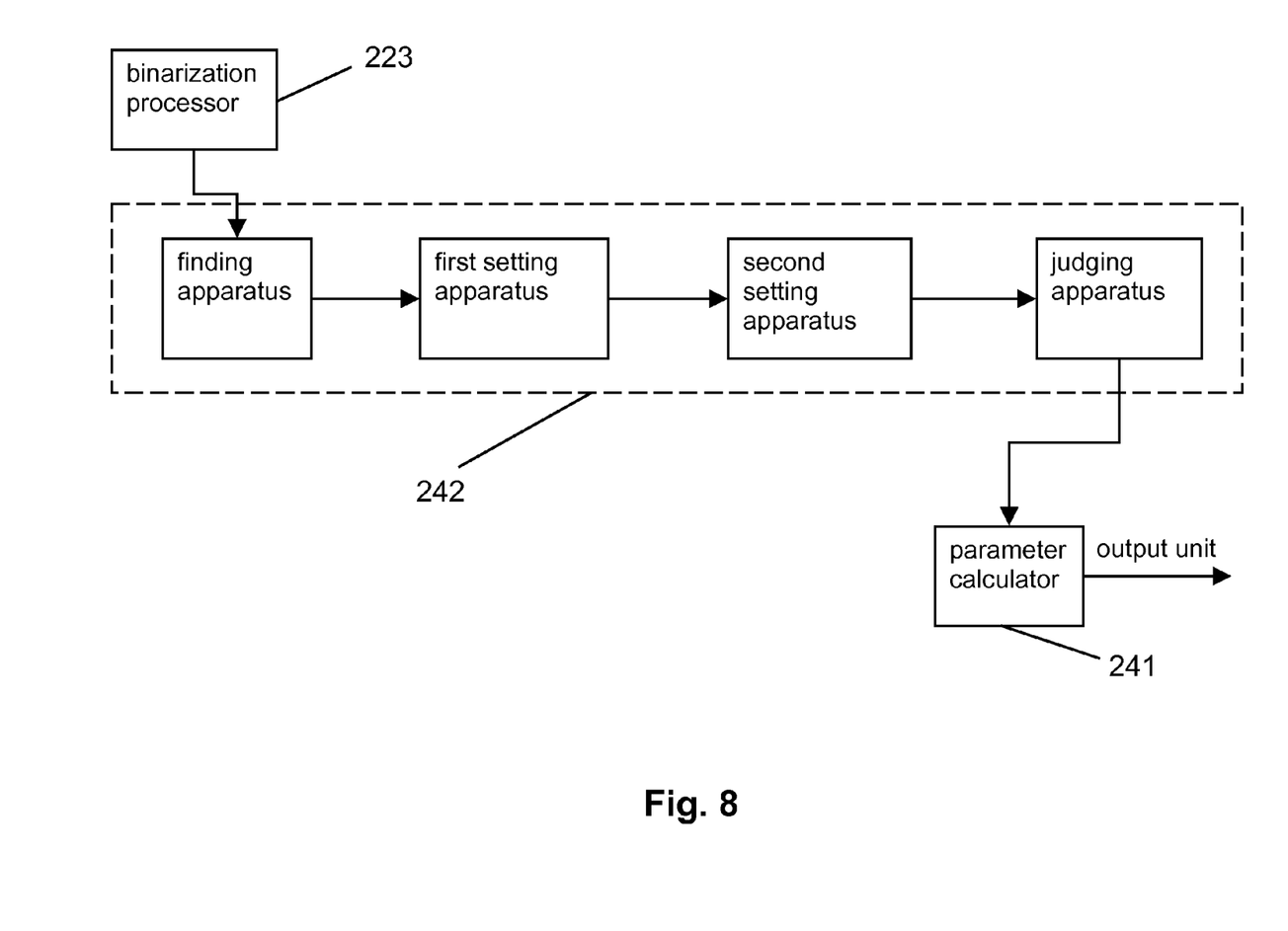
FIG. 8 shows a schematic illustration of the second embodiment of the estimation unit of the medical device of FIG. 6.

As showing in FIG. 8, the estimator 242 further comprises a second setting apparatus which is connected between the first setting apparatus and the judging apparatus. If the ACD values of immediate neighbors of each of the foreground voxel are not greater than the transition threshold, the second setting apparatus sets the neighbors as foreground voxels.

Figure 9:
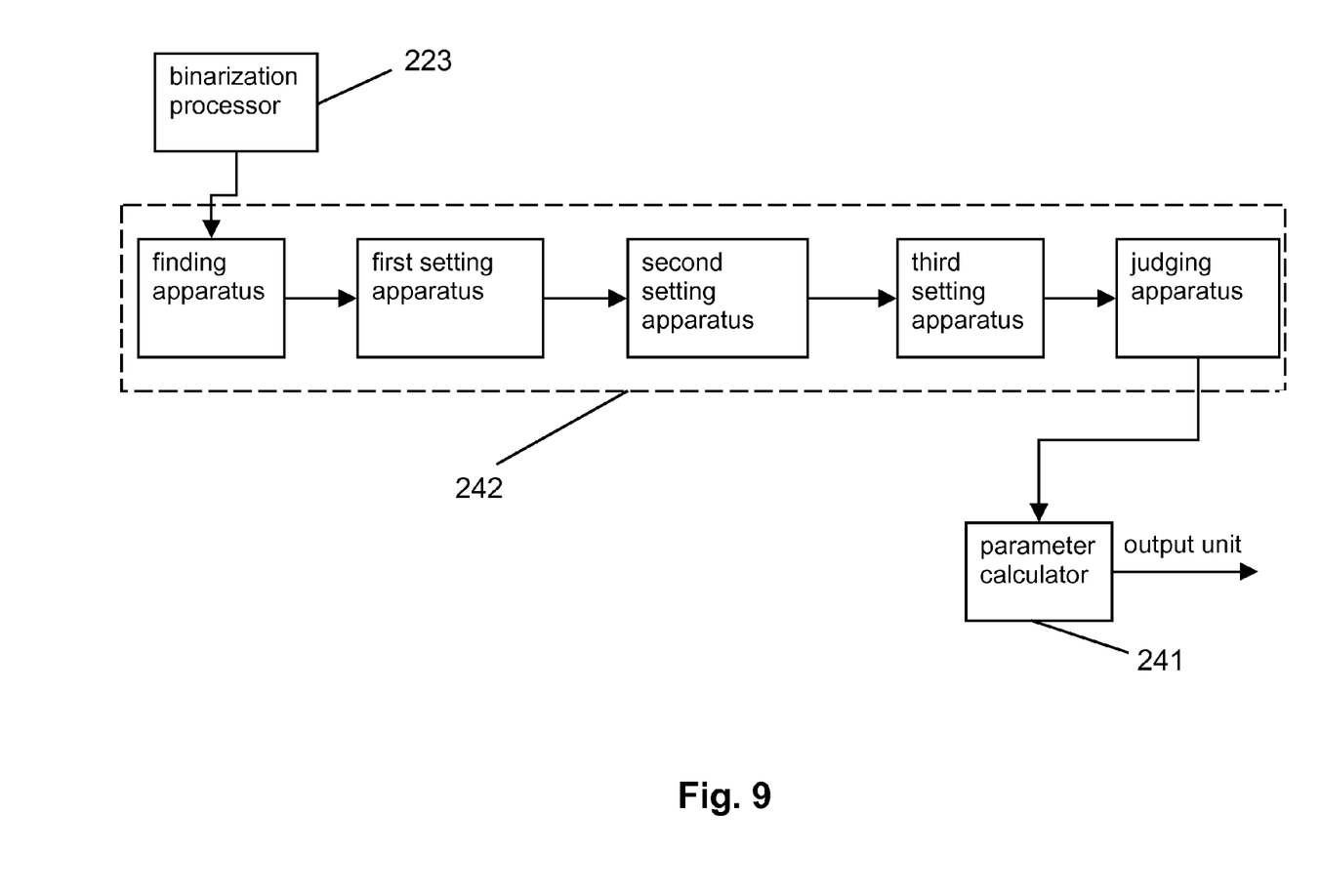
FIG. 9 shows a schematic illustration of the third embodiment of the estimation unit of the medical device of FIG. 6.
Figure 10:
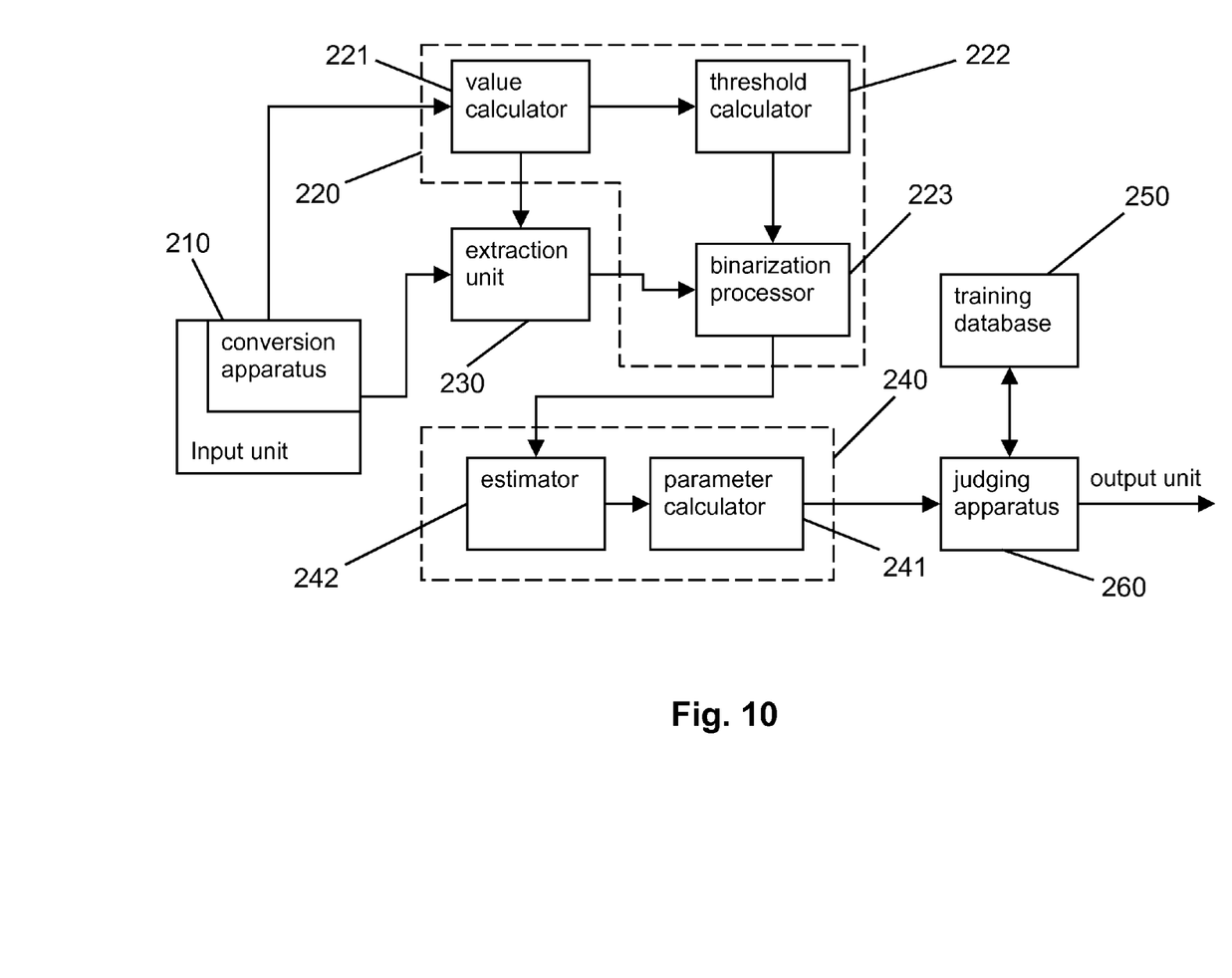
FIG. 10 shows a schematic illustration of the medical device for producing and assessing data of the suitability for thrombolysis of a patient according to the present invention.

As showing in FIG. 9, the estimator 242 further comprises a third setting apparatus sets a foreground component to a background component if the volume of the foreground component is smaller than a third predefined volume.

EXAMPLE 3

The Method for Producing and Assessing Data of the Suitability for Thrombolysis of a Patient The method of the present invention comprises a group of steps in which the first step to the five step are the same as example 1 and the sixth step to the seven step are as follows:

Step #6: Assessing if There Exist Ischemic Tissues to be Rescued

To assess if there exist ischemic tissues to be rescued is to see if the transition regions contain ischemic tissues to be rescued. This is achieved through training samples. A patient's data is used as one of the training samples if it meets one of the following criteria: 1) the patient shows substantial improvement after thrombolysis, which implies that this patient has ischemic tissues to be rescued and these tissues have been rescued through thrombolysis; 2) the patient symptoms are deteriorated after thrombolysis, which implies that this patient should not be handled with thrombolysis; and 3) those patients that show no mismatch by the traditional DWI-PWI method should correspond to no tissues to be rescued.

The parameters pertaining to the transition regions of Cmt1 (x, y, z) and Cmt2(x, y, z), i.e., $\delta ADC_1$, $\delta ADC_2$, $(R_{11}-R_{10})$, $(R_{21}-R_{20})$, $avgGradN_1$, $avgGradN_2$, as well as the volumes of approximated core and transition regions (volCore and numCore) can be employed for training. One of the possible assessing criteria could be: when the maximum of $\delta ADC_1$ and $\delta ADC_2$ is smaller than 0.21 (with ($thADC_2$ (z)-$thADC_1$ (z)) being 0.20), or when volCore is larger than 100 ml, there will be no ischemic tissues to be rescued.

Step #7: Assessing the Suitability for Thrombolysis

To evaluate if a patient is suitable for thrombolysis, the decision rules can be derived from training samples as done in step #6. A patient's data is used as one of the training samples if it meets one of the following criteria: 1) the patient shows substantial improvement after thrombolysis, which implies that this patient is suitable for thrombolysis; 2) the patient symptoms are deteriorated after thrombolysis, which implies that this patient is not suitable for thrombolysis; and 3) those patients show symptomatic brain hemorrhage after thrombolysis are not suitable for thrombolysis.

The parameters pertaining to the approximated core and transition regions of Cmt1(x, y, z) and Cmt2(x, y, z) are employed to build up the rules are: $\delta ADC_1$, $\delta ADC_2$, $(R_{11}-R_{10})$, $(R_{21}-R_{20})$, $avgGradN_1$, $avgGradN_2$, $avgCoreADC_1$, $avgCoreADC_2$, $sdCoreADC_1$, $sdCoreADC_2$, $cvCoreADC_1$, $cvCoreADC_2$, and the approximated volumes of core transition regions volCore, numCore. A possible rule for thrombolysis is: when there are tissues to be rescued (judged from step #6) and the maximum of $cvCoreADC_1$ and $cvCoreADC_2$ is smaller than 0.10.

EXAMPLE 4

Figure 11:
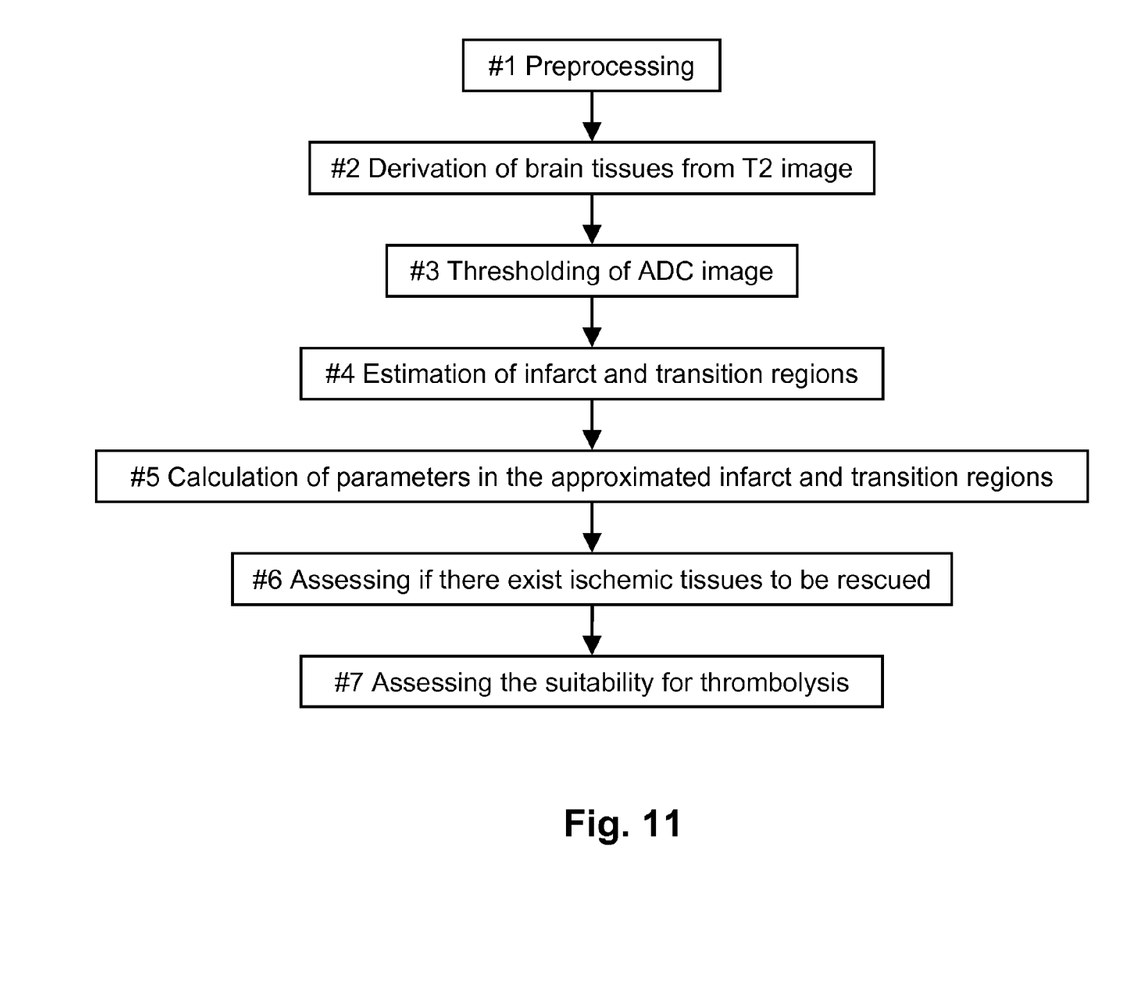
FIG. 11 shows a simplified flowchart of the method for producing and assessing data of the suitability for thrombolysis of a patient according to the present invention.

The A Medical Device Producing and Assessing Data of the Suitability for Thrombolysis of a Patient A computer assisted diagnosis system to decide suitability of thrombolysis comprises at least a computer, an input unit, a processing module, and an output unit. The computer provides interface for inputting the DICOM data of the patients T2(x, y, z) and ADC(x, y, z), the processing unit to perform the processing described in steps #1 to #7, and the output unit to output the processed ADC (like marking those approximated core and transition regions as shown in FIG. 5) and the recommendation for thrombolysis according to the result of step #7, see FIG. 11. Based on the device described in EXAMPLE 1, the medical device of EXAMPLE 4 further comprises a training database and an output unit connected to the parameter calculator and the training database respectively.

Although only limited example embodiments are described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing volumetric parameters associated with brain tissue of a patient, the method comprising:
    obtaining diffusion weighted imaging of a patient comprising of a T2-weighted image and an apparent diffusion coefficient (ADC) image;
    differentiating non-brain tissues and said brain tissue in said T2-weighted image;
    obtaining a brain tissue image without said non-brain tissues from said T2-weighted image;
    defining a core ADC threshold and a transition ADC threshold that could differentiate a core region and a transition region respectively;
    binarizing said apparent diffusion coefficient image with said transition ADC threshold according to said brain tissue image to achieve a binarized ADC image;
    determining said core region and said transition region in said binarized ADC image; and
    calculating a plurality of volumetric parameters in said core region and said transition region.

2. The method as claimed in claim 1, wherein during said loading step, said images being 16-bit image data are converted to 8-bit data.

3. The method as claimed in claim 1, wherein said extracting step comprises:
    defining a intensity threshold excluding non-brain tissues from said T2-weighted image through fuzzy c-means clustering;
    binarizing said T2-weighted image to obtain a binarized T2 image in which any voxel whose value is not smaller than said intensity threshold is set as foreground voxel and other voxels are set as background voxels;
    finding the largest foreground connected component of said binarized T2 image;
    applying morphological open to the largest foreground connected component of said binarized T2 image;
    finding the foreground regions of said binarized T2 image; and
    changing the holes which are the background regions enclosed by the foreground region into the foreground.

4. The method as claimed in claim 1, wherein said achieving step comprises:
    getting a ADC value of the normal brain tissue from said apparent diffusion coefficient image; and
    obtaining said core and transition ADC thresholds through multiplying said ADC value of the normal brain tissue by two constants respectively.

5. The method as claimed in claim 4, wherein said getting step comprises:

finding a value $ADC_{max}$ which is the most frequent ADC value in said apparent diffusion coefficient image from all brain tissue according to said brain tissues image; and taking a value in the neighborhood of said $ADC_{max}$ as a value $ADC_{ref}$ which is an approximation of said ADC value of the normal brain tissue.

6. The method as claimed in claim 5, wherein during said getting step said ADC value of the normal brain tissue is slice dependent and can be achieved by finding the most frequent ADC value of the brain tissues for each slice and taking the value in the neighborhood of the most frequent ADC value for each slice, during said obtaining step said core and transition ADC thresholds are also slice dependent, during said binarizing step said apparent diffusion coefficient images of each slice are binarized with said core and transition ADC thresholds of each slice.

7. The method as claimed in claim 1, wherein during said binarizing step, a plurality of voxels whose ADC values are not greater than said transition threshold are set as the foreground voxels, and the other voxels are set as the background voxels.

8. The method as claimed in claim 1, wherein during said estimating step, a foreground component in said binarized ADC image will be set to a background component if the volume of said foreground component is smaller than a first volume or the volume of voxels whose ADC values are smaller than said core ADC value in said foreground component is smaller than a second predefined volume, and for each of said foreground components in said binarized ADC image, those voxels with ADC values smaller than said core threshold form said core region while those voxels with ADC values smaller than said transition threshold and bigger than said core threshold form said transition region.

9. The method as claimed in claim 8, wherein during said estimating step, a foreground component will be set to a background component if the maximum distance of said foreground component to the brain boundary is not smaller than 10 mm.

10. The method as claimed in claim 8, wherein during said estimating step, if the ACD values of immediate neighbors of each of the voxel in said foreground component are not greater than said transition threshold, said neighbors are set as foreground voxels.

11. The method as claimed in claim 10, wherein during said estimating step, said foreground component will be set to a background components if the volume of said foreground component is smaller than a third predefined volume.

12. The method as claimed in claim 7, wherein during said calculating step, among all the foreground components in said binarized ADC image, find at least one connected component with the maximum volume and calculate said parameters of said core region and said transition region in said connected component.

13. The method as claimed in claim 12, wherein said calculating step comprises a calculation of a ADC gradient of said transition region, said calculation of said ADC gradient comprising:
finding the internal points of said connected component with the maximum volume;
calculating the ADC gradient of each internal point;
calculating the average ADC gradients of said connected component with the maximum volume denoted as avgGrad;
calculating the average ADC values of all voxels whose ADC values are in the range of said core threshold and said transition threshold denoted as avgTRADC;
calculating the normalized ADC gradient of said transition region which is determined by the following formula $avgGradN = avgGrad*C/(ADC_{ref}*avgTRADC)$ where C is a constant for normalization and $ADC_{ref}$ is a ADC value of the normal brain tissue.

14. The method as claimed in claim 13, wherein during said calculation of the ADC gradient of said transition region, find the components with the maximum and second maximum volumes, calculate the normalized ADC gradients of the two components respectively, the ADC gradient of the transition region is the maximum of the normalized ADC gradients of the two components.

15. The method as claimed in claim 13, wherein said calculating step further comprises a calculation of the radial distance of said transition region comprising:
calculating the number of voxels whose ADC values are not greater than said core threshold denoted as $N_0$;
calculating the number of voxels whose ADC values are in the range of said core and transition thresholds denoted as $N_1$;
calculating the radial dimensions of said core and transition regions which is determined by the following formulae $R_0 = sqrt(N_0/\pi)$ and $R_1 = sqrt((N_0+N_1)/\pi)$; and
calculating the radial distance of said transition region by subtracting $R_0$ from $R_1$.

16. The method as claimed in claim 15, wherein during said calculation of the radial distance of said transition region, find the components with the maximum and second maximum volumes, calculate the radial distances of the two components respectively, then the radial distance is the maximum of the radial distances of the two components.

17. The method as claimed in claim 15, wherein said calculating step further comprises a calculation of the ADC change of said transition region which is defined as the product of the radial distance and the normalized average gradient of said transition region.

18. The method as claimed in claim 17, wherein during said calculation the ADC change of said transition region, find the components with the maximum and second maximum volumes, calculate the ADC changes of the two components respectively, then the ADC change of said transition region is the minimum of the ADC changes of the two components.

19. The method as claimed in claim 11, wherein said calculating step further comprises a calculation of the coefficient of variation of ADC which is determined by the following formula $cvCoreADC = sdCoreADC/avgCoreADC$ where avgCoreADC, sdCoreADC and cvCoreADC are the average, standard deviation and coefficient of variation of ADC for all voxels whose ADC values are not greater than said core threshold.

20. A medical device for producing volumetric parameters associated with brain tissues of a patient, the device comprising:
an input unit obtaining two diffusion weighted images: (1) a T2-weighted image, and (2) an Apparent Diffusion Coefficient (ADC) image;
an extraction unit extracting a brain tissues image from said T2-weighted image;
an image processing unit utilizing a core ADC threshold and a transition ADC threshold that could differentiate a core region and a transition region respectively and binarizing said Apparent Diffusion Coefficient image through applying said transition ADC threshold according to said brain tissues image to achieve a binarized ADC image; and an estimation unit determining a core region and a transition region in said binarized ADC image and calculating a volumetric plurality of parameters in said core region and said transition region.

21. The medical device as claimed in claim 20, wherein said input unit has a conversion apparatus converting said image from 16-bit data to 8-bit data.

22. The medical device as claimed in claim 20, wherein said image processing unit comprises:
a value calculator connected to the input unit and the extraction unit and getting a ADC value of the normal brain tissue from the ADC image;
a threshold calculator multiplying the ADC value of the normal brain tissue by two constants respectively to achieve a core ADC threshold and a transition ADC threshold that could differentiate a core region and a transition region respectively; and
a binarization processor binarizing the ADC image through the transition ADC threshold according to the brain tissues image to achieve a binarized ADC image.

23. The medical device as claimed in claim 20, wherein said estimation unit comprises:
an estimator determining a core region and a transition region in said binarized ADC image; and
a parameter calculator finding at least one foreground connected component with the maximum volumes in the core region and the transition region and calculating said plurality of volumetric parameters in the components.

24. The medical device as claimed in claim 20, wherein said estimator comprises:
a finding apparatus finding a foreground component in the binarized ADC image of each slice;
a first setting apparatus setting a foreground component to a background component if the volume of the foreground component is smaller than a first volume and the volume of voxels whose ADC values are smaller than the core ADC value is smaller than a second predefined volume; and
a judging apparatus determining those voxels with ADC values smaller than the core threshold forming the core region while those voxels with ADC values smaller than the transition threshold and bigger than the core threshold forming the transition region.

25. The medical device as claimed in claim 24, wherein said estimator further comprises a second setting apparatus which is connected between the first setting apparatus and the judging apparatus, setting the immediate neighbors of each of the foreground voxel as foreground voxels if the ACD values of said neighbors are not greater than the transition threshold.

26. The medical device as claimed in claim 24, wherein said estimator further comprises a third setting apparatus setting a foreground component to a background component if the volume of the foreground component is smaller than a third predefined volume.

27. A medical device for producing and assessing data of the suitability for thrombolysis of a patient, the device comprising:

an input unit obtaining two diffusion weighted images: (1) a T2-weighted image, and (2) an Apparent Diffusion Coefficient (ADC) image;
an extraction unit extracting a brain tissues image from said T2-weighted image;
an image processing unit utilizing a core ADC threshold and a transition ADC threshold that could differentiate a core region and a transition region respectively and binarizing said Apparent Diffusion Coefficient image through applying said transition ADC threshold according to said brain tissues image to achieve a binarized ADC image;
an estimation unit determining a core region and a transition region in said binarized ADC image and calculating a plurality of volumetric parameters in said core region and said transition region;
a training database having training samples using similar patient data; and
an output unit assessing the existence of the ischemic tissues to be rescued and the suitability for thrombolysis if said parameters accord with predetermined rules derived from said training samples.

28. The medical device as claimed in claim 27, wherein said predetermined rules are about an ADC change of the transition region, volumes of the core region, and coefficient of variation of ADC.

29. A method for producing and assessing data of the suitability for thrombolysis of a patient, the method comprising:
obtaining diffusion weighted imaging of a patient comprising a T2-weighted image and an apparent diffusion coefficient (ADC) image;
differentiating non-brain tissues and brain tissue in said T2-weighted image;
obtaining a brain tissue image without said non-brain tissues from said T2-weighted image;
defining a core ADC threshold and a transition ADC threshold that could differentiate a core region and a transition region respectively;
binarizing said apparent diffusion coefficient image with said transition ADC threshold according to said brain tissue image to achieve a binarized ADC image;
determining said core region and said transition region in said binarized ADC image;
calculating a plurality of volumetric parameters in said core region and said transition region; and
assessing the existence of the ischemic tissues to be rescued and the suitability for thrombolysis if said parameters accord with predetermined rules derived from training samples.

30. The medical device as claimed in claim 29, wherein said predetermined rules are about an ADC change of the transition region, volume of the core region, and coefficient of variation of ADC.

* * * * *